United States Patent
Dwivedi et al.

(10) Patent No.: US 9,951,009 B2
(45) Date of Patent: Apr. 24, 2018

(54) POLYMORPHIC FORM OF PYRROLE DERIVATIVE AND INTERMEDIATE THEREOF

(71) Applicant: CADILA HEALTHCARE LIMITED, Ahmedabad, Gujarat (IN)

(72) Inventors: Shri Prakash Dhar Dwivedi, Gujarat (IN); Ramesh Chandra Singh, Gujarat (IN); Vikas Patel, Gujarat (IN); Amar Rajendra Desai, Gujarat (IN)

(73) Assignee: Cadila Healthcare Limited, Ahmedabad, Gujarat (IN)

( * ) Notice: Subject to any disclaimer, the term of this patent is extended or adjusted under 35 U.S.C. 154(b) by 0 days.

(21) Appl. No.: 14/915,457

(22) PCT Filed: Aug. 28, 2014

(86) PCT No.: PCT/IN2014/000551
§ 371 (c)(1),
(2) Date: Feb. 29, 2016

(87) PCT Pub. No.: WO2015/029066
PCT Pub. Date: Mar. 5, 2015

(65) Prior Publication Data
US 2016/0207884 A1    Jul. 21, 2016

(30) Foreign Application Priority Data
Aug. 29, 2013  (IN) .......................... 2828/MUM/2013

(51) Int. Cl.
*C07D 207/333* (2006.01)
*C07D 207/325* (2006.01)

(52) U.S. Cl.
CPC ..... *C07D 207/333* (2013.01); *C07D 207/325* (2013.01)

(58) Field of Classification Search
CPC .................. C07D 207/325; C07D 207/333
See application file for complete search history.

(56) References Cited

U.S. PATENT DOCUMENTS

| | | |
|---|---|---|
| 6,987,132 B1 | 1/2006 | Zaleski et al. |
| 7,041,837 B2 | 5/2006 | Lohray et al. |
| 7,323,491 B2 | 1/2008 | Lohray et al. |
| 8,110,598 B2 | 2/2012 | Lohray et al. |
| 8,212,057 B2 | 7/2012 | Lohray et al. |
| 2011/0275669 A1 | 11/2011 | Lohray et al. |

FOREIGN PATENT DOCUMENTS

| | | | |
|---|---|---|---|
| WO | 2003/009841 A1 | | 2/2003 |
| WO | 2012/104869 A1 | | 8/2012 |
| WO | WO 2012/104869 | * | 8/2012 |
| WO | 1910/MUM/2013 A | | 5/2013 |
| WO | 2014/195967 A2 | | 12/2014 |

\* cited by examiner

*Primary Examiner* — Valerie Rodriguez-Garcia
(74) *Attorney, Agent, or Firm* — Goodwin Procter LLP

(57) ABSTRACT

The present invention relates to Saroglitazar free acid of Formula (IA) or its pharmaceutically acceptable salts, pharmaceutically acceptable solvates, pharmaceutically acceptable esters, stereoisomers, tautomers, analogs and derivatives thereof. The present invention also provides an amorphous form of saroglitazar free acid and processes of preparation thereof. The present invention also provides pharmaceutical composition comprising an amorphous form saroglitazar magnesium.

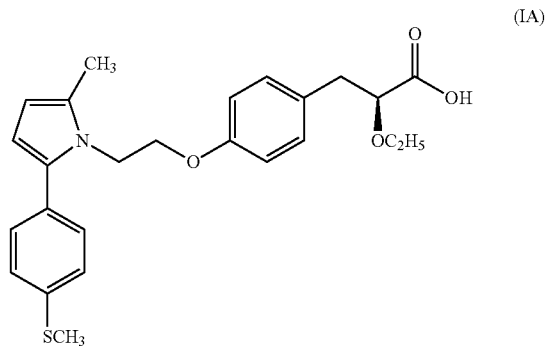

(IA)

4 Claims, 5 Drawing Sheets

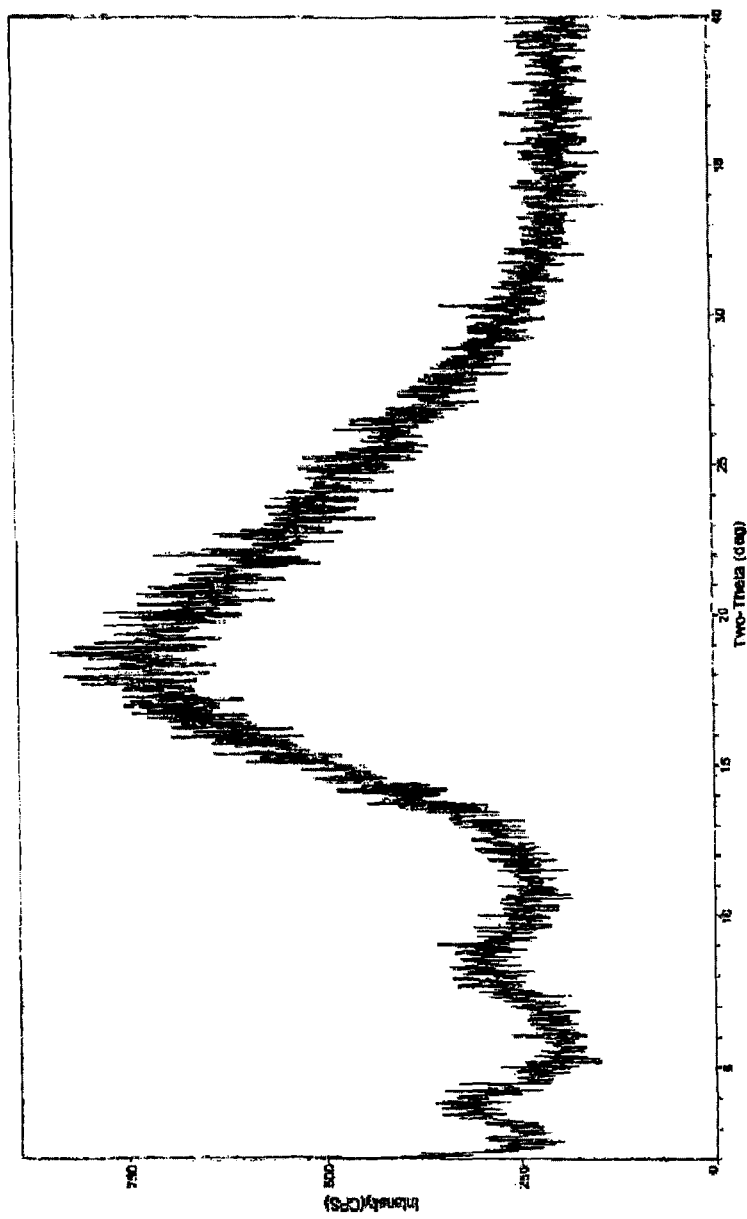

POLYMORPHIC FORM OF PYRROLE DERIVATIVE AND INTERMEDIATE THEREOF

RELATED APPLICATION

Figure 1:
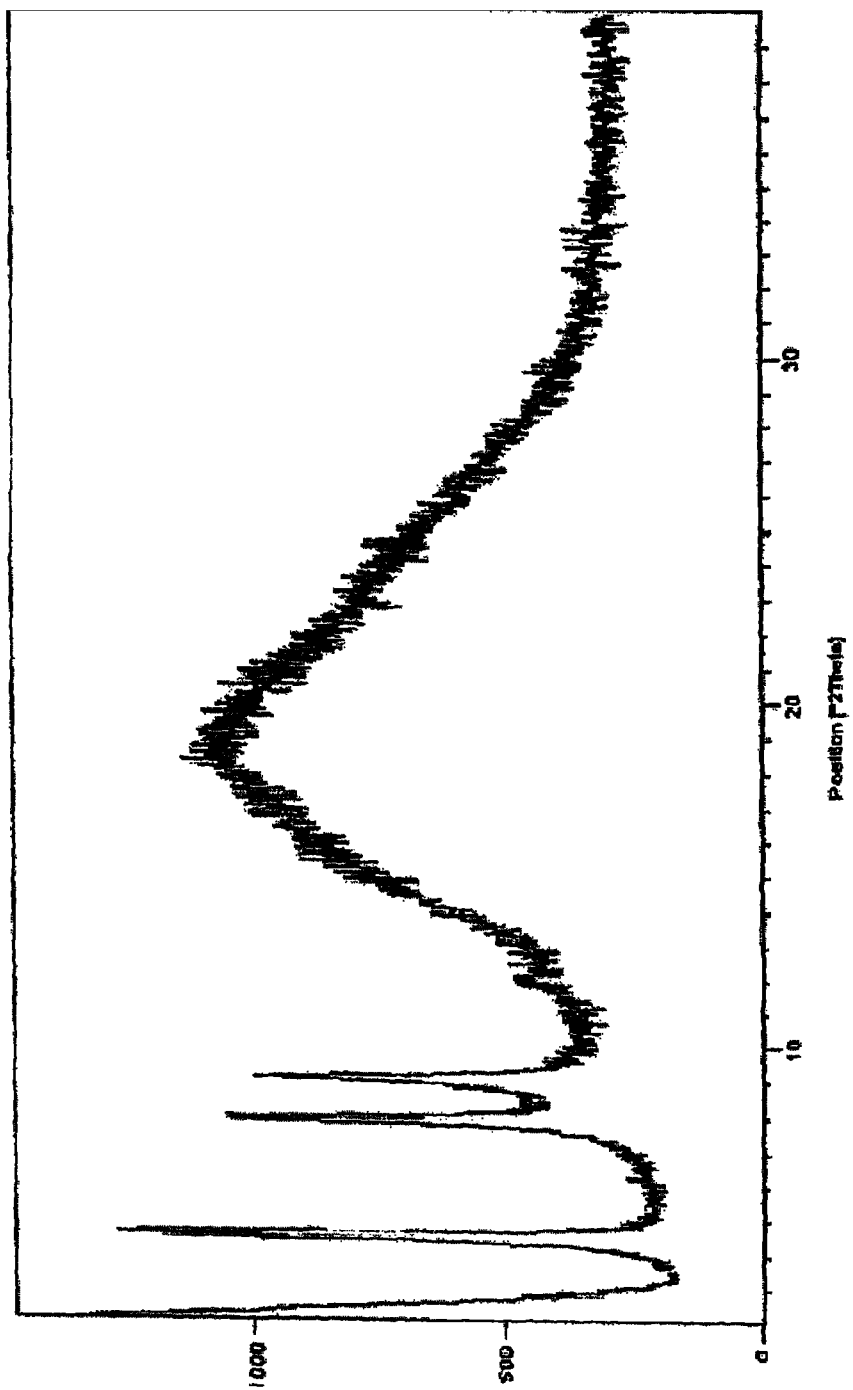

This application is a national phase entry under 35 USC 371 of International Patent Application No.: PCT/IN2014/000551 filed on 28 Aug. 2014, which claims priority from Indian Application No. 2828/MUM/2013 filed on 29 Aug. 2013, the disclosures of which are incorporated in their entirety by reference herein.

FIELD OF THE INVENTION

The present invention relates to polymorphic form of pyrrole derivative and intermediate thereof. In particular, the invention relates to pyrrole derivative having hypolipidemic hypocholesteremic activities. More particularly, the invention relates to an amorphous form of saroglitazar magnesium and processes for its preparation. The invention further relates to the pharmaceutical composition comprising an amorphous form saroglitazar magnesium useful as anti-hypolipidemic anti-hypocholesteremic agent.

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

Pyrrole derivative of present invention is chemically 2-ethoxy-3-(4-(2-(2-methyl-5-(4-(methylthio)phenyl)-1H-pyrrol-1-yl)ethoxy)phenyl)propanoate, which may be optically active or racemic and its pharmaceutically acceptable salts, hydrates, solvates, polymorphs or intermediates thereof. The INN name for pyrrole derivative is Saroglitazar® which is magnesium salt of pyrrole compound of Formula (I), having below chemical structure.

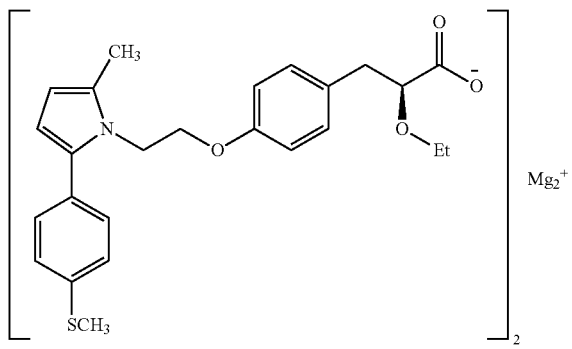

(I)

The compound of Formula (I) lower or modulate triglyceride levels and/or cholesterol levels and/or lower density lipoproteins (LDL) and raise HDL plasma levels and hence are useful in combating different medical conditions, where such lowering (and raising) is beneficial. Thus, it could be used in the treatment and/or prophylaxis of obesity, hyperlipidemia, hypercholesteremia, hypertension, atherosclerotic disease events, vascular restenosis, diabetes and many other related conditions. The compound of Formula (I) are useful to prevent or reduce the risk of developing atherosclerosis, which leads to diseases and conditions selected from arteriosclerotic cardiovascular diseases, stroke, coronary heart diseases, cerebrovascular diseases, peripheral vessel diseases and related disorders.

U.S. Pat. No. 6,987,123 B2 (the US '123 patent) discloses novel heterocyclic compounds, their preparation, pharmaceutical compositions containing them and their use in medicine. The US '123 patent discloses five reaction pathways for the synthesis of pyrrole derivatives.

In route-1 the compound of Formula (1a) and (1b) are reacted under Paal-Knoor conditions to obtain compound (1) as shown below:

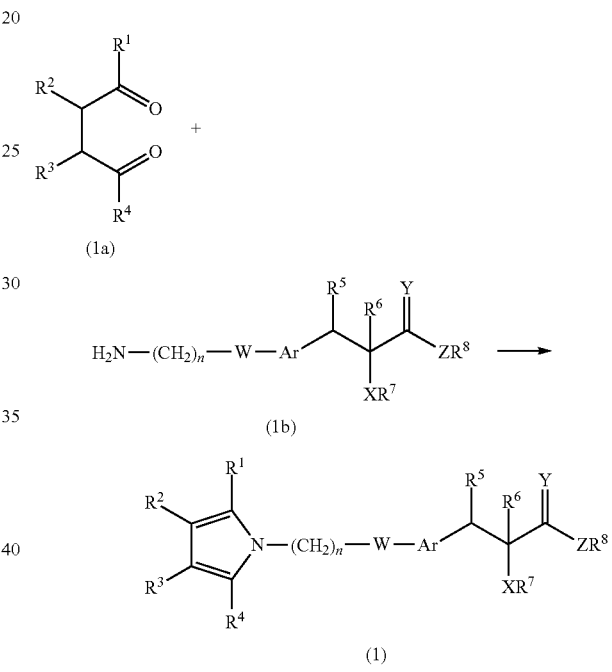

In route-2 the compound of Formula (1c) and (1d) are reacted in presence of base in suitable organic solvent to obtain the compound (1) as shown below:

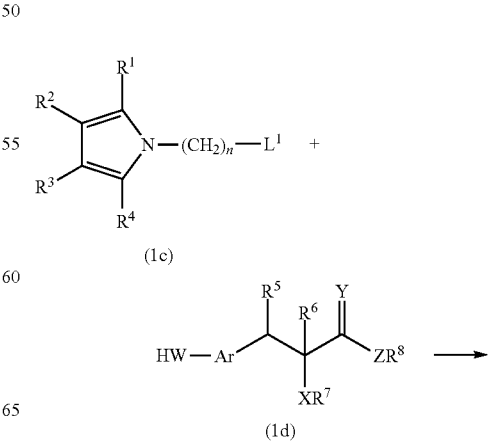

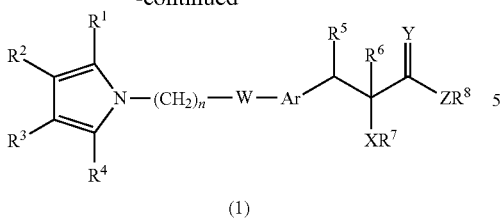

(1)

In route-3 the compound of Formula (1e) and (1d) are reacted in presence of coupling agents like DCC, EDC etc. to obtain the compound (1) as shown below:

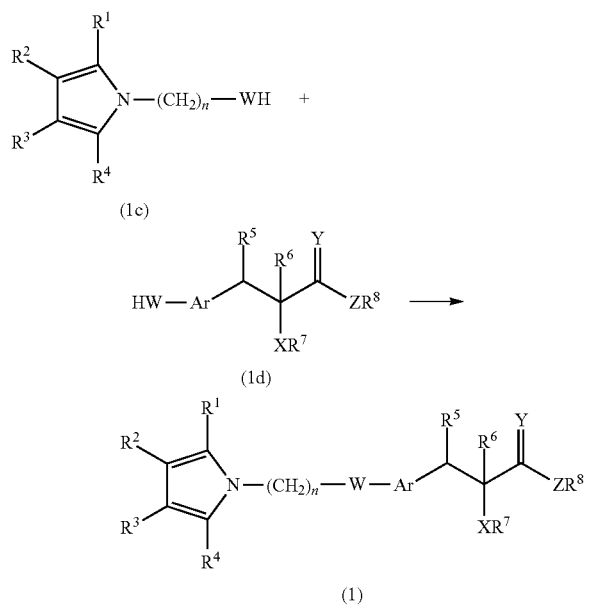

In route-4 the compound of Formula (1f) and (1g) are reacted in presence of rhodium salts such as rhodium (II) acetate in suitable solvents like benzene, toluene, ether, THF, dioxane and the like to obtain the compound (1) as shown below:

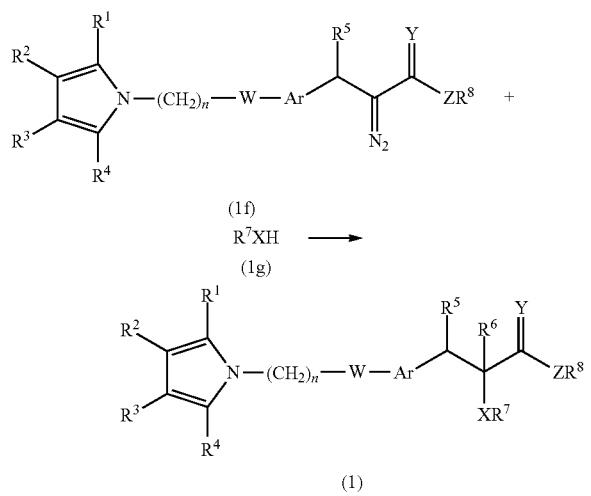

In route-5 the compound of Formula (1e) and (1d) are reacted under Wittig Homer conditions to obtain the compound (1) as shown below:

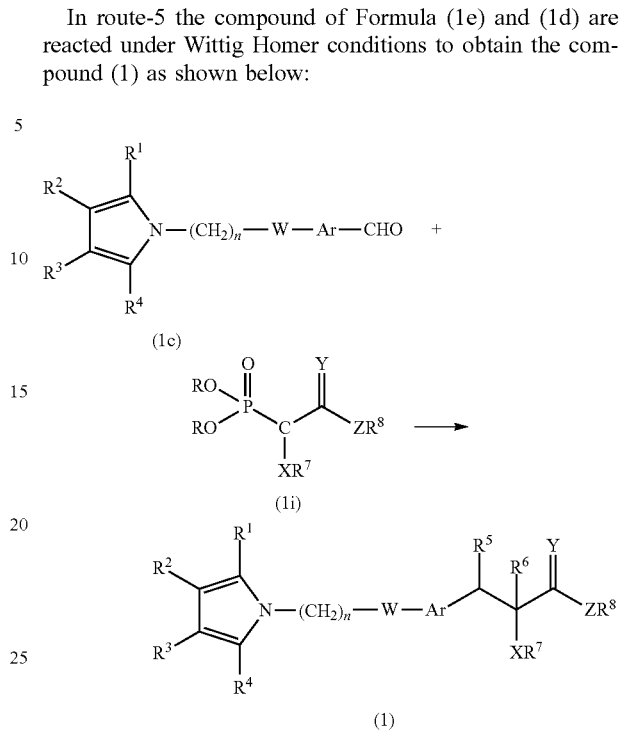

U.S. Pat. Nos. 7,041,837 B2, 7,323,491 B2, 8,110,598 B2, 8,212,057 B2 discloses different pyrrole derivative of Formula (1) and their intermediates.

2011/0275669 A1 discloses the process for the preparation of pyrrole derivative of general Formula (1) prepared by the five reaction pathways as disclosed herein above.

WO 2012/104869 A1 provides the use of compound of Formula (I) for the treatment of lipodystrophy.

Our own co-pending application IN 1910/MUM/2013 A discloses substantially amorphous saroglitazar magnesium having percentage crystallinity less than 25% and process for its preparation, which is incorporated herein as reference.

WO 2012/104869 A1, provides the use of compound of Formula (1) for the treatment of lipodystrophy.

The different physical properties exhibited by polymorphs affect important pharmaceutical parameters selected from storage, stability, compressibility, density and dissolution rates (important in determining bioavailability). Stability differences may result from changes in chemical reactivity (e.g., differential hydrolysis or oxidation, such that a dosage form discolors more rapidly when comprised of one polymorph than when comprised of another polymorph), mechanical changes (e.g., tablets crumble on storage as a kinetically favored crystalline form converts to thermodynamically more stable crystalline form) or both (e.g., tablets of one polymorph are more susceptible to breakdown at high humidity). Solubility differences between polymorphs may, in extreme situations, result in transitions to crystalline forms that lack potency or are toxic. In addition, the physical properties of the crystalline form to that of an amorphous form may be important in pharmaceutical processing. For example, an amorphous form may provide better bioavailability than the crystalline form. Thus, a present amorphous form may be useful for formulations which can have better stability, solubility, storage, compressibility etc important for formulation and product manufacturing and doesn't degrade to crystalline forms of saroglitazar.

Therefore, it is desirable to have amorphous form of drugs with high purity to meet the regulatory requirements and also highly reproducible processes for their preparation.

In view of the above, it is therefore, desirable to provide an efficient, more economical, less hazardous and eco-friendly process for the preparation of amorphous saroglitazar having no crystallinity. The process disclosed in the prior art provides substantially amorphous having presence of crystallinity. However, the present amorphous form of saroglitazar magnesium may provide at least a suitable alternative for development of finished formulations.

SUMMARY OF THE INVENTION

In one general aspect, there is provided saroglitazar free acid of Formula (IA) or its pharmaceutically acceptable salts, pharmaceutically acceptable solvates, pharmaceutically acceptable esters, stereoisomers, tautomers, analogs and derivatives thereof.

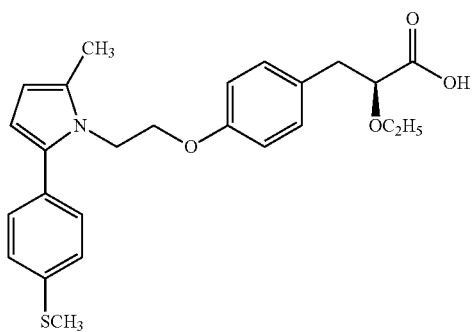

(IA)

In another general aspect, there is provided an amorphous form of saroglitazar free acid of Formula (IA).

In another general aspect, there is provided an amorphous form of saroglitazar magnesium of Formula (I).

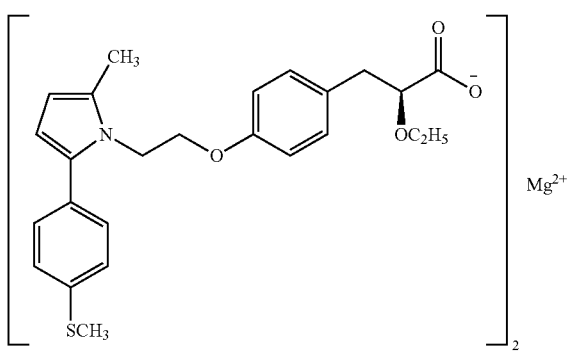

(I)

In another general aspect, there is provided a process for the preparation of an amorphous form of saroglitazar magnesium of Formula (I),

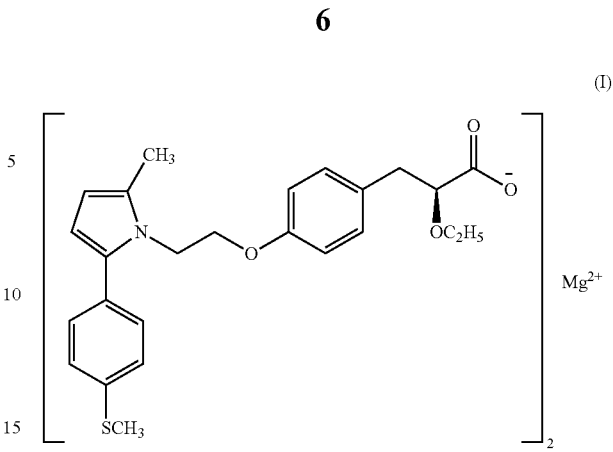

(I)

the process comprising:

(a) dissolving saroglitazar magnesium of Formula (I) in one or more organic solvents to obtain a solution, (b) adding the solution in one or more of anti-solvent at temperature from about −80° C. to about 150° C. to obtain saroglitazar magnesium of Formula (I); and (c) obtaining the amorphous saroglitazar magnesium by removal of anti-solvent.

In another general aspect, there is provided a process for the preparation of an amorphous form of saroglitazar magnesium of Formula (I),

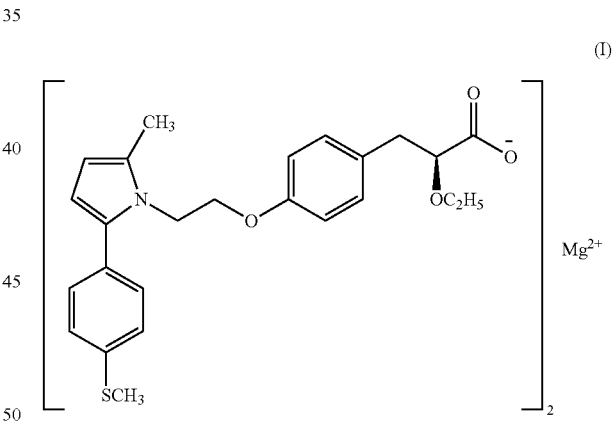

(I)

the process comprising:

(a) reacting a hydroxy compound (A) with a mesylate compound (A1) in one or more organic solvents in the presence of a base to obtain an alkoxy ester compound of Formula (II),

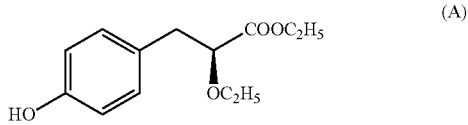

(A)

-continued

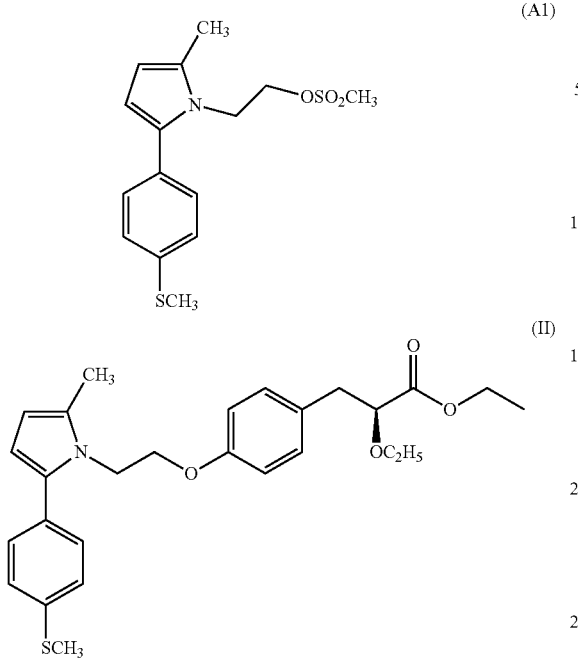

(b) hydrolyzing the alkoxy ester compound of Formula (II) with a base in one or more organic solvents to obtain a reaction mixture,
(c) washing the reaction mixture with one or more organic solvents to obtain aqueous layer,
(d) treating the aqueous layer with magnesium source to obtain saroglitazar magnesium solution,
(e) removal of solvent from the solution to obtain saroglitazar magnesium residue; and
(f) addition of one or more of anti-solvent to the residue followed by removal of anti-solvent to obtain the amorphous form of saroglitazar magnesium of Formula (I).

In another general aspect, there is provided a process for the preparation of saroglitazar free acid of Formula (IA) or its pharmaceutically acceptable salts thereof,

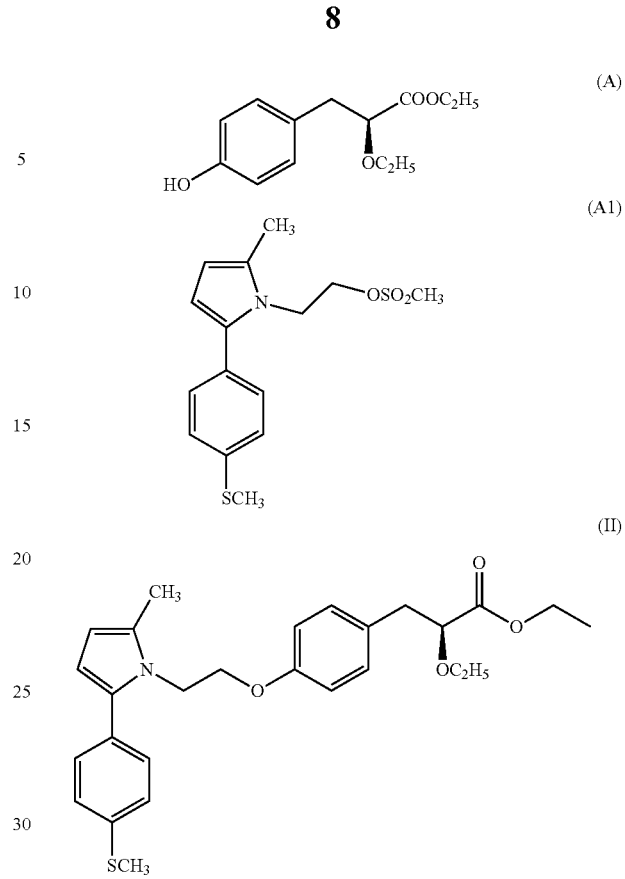

(b) hydrolyzing the alkoxy ester compound of Formula (H) with a base in one or more organic solvent to obtain reaction mixture,
(c) acidifying the reaction mixture with an acid to obtain saroglitazar free acid (IA) in reaction mixture,
(d) extracting the saroglitazar free acid (IA) in one or more organic solvents; and
(e) obtaining the saroglitazar free acid (IA) by removal of solvent.

In another general aspect, there is provided a process for the preparation of saroglitazar free acid of Formula (IA) or its pharmaceutically acceptable salts thereof,

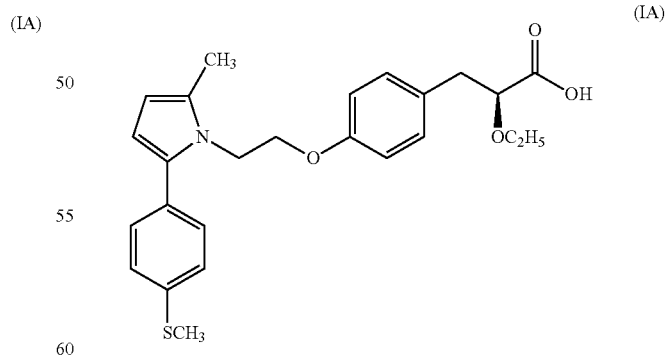

the process comprising:
(a) reacting a hydroxy compound (A) with a mesylate compound (A1) in one or more organic solvents in the presence of a base to obtain alkoxy ester compound of Formula (II), the process comprising:
(a) providing a solution of saroglitazar magnesium of Formula (I) in one or more organic solvents,
(b) adding a base in the solution to obtain a reaction mixture,
(c) acidifying the reaction mixture with an acid to obtain saroglitazar free acid (IA) in reaction mixture, (d) extracting the saroglitazar free acid (IA) in one or more organic solvents; and
(e) obtaining the saroglitazar free acid (IA) by removal of solvent.

In another general aspect, there is provided an amorphous form of saroglitazar magnesium having particle size distributions having D(10) of about 20 μm or less, (D50) of about 100 μm or less, and D(90) of about 200 μm or less, or any combination thereof.

In another general aspect, there is provided an amorphous form of saroglitazar magnesium having a purity of at least about 98% by area percentage of HPLC. In particular, saroglitazar magnesium having a purity of at least about 99%, more particularly, a purity of at least about 99.5%, further more particularly, a purity of at least about 99.8%, most particularly, a purity of at least about 99.9% by area percentage of HPLC.

In another general aspect, there is provided an amorphous form of saroglitazar magnesium having a chiral purity of at least about 98% by area percentage of HPLC. In particular, saroglitazar magnesium having a chiral purity of at least about 99%, more particularly, a purity of at least about 99.5%, further more particularly, a purity of at least about 99.8%, most particularly, a purity of at least about 99.9% by area percentage of HPLC.

In another general aspect, there is provided saroglitazar free acid of Formula (IA) having a purity of at least about 98% by area percentage of HPLC. In particular, saroglitazar free acid having a purity of at least about 99%, more particularly, a purity of at least about 99.5%, further more particularly, a purity of at least about 99.8%, most particularly, a purity of at least about 99.9% by area percentage of HPLC.

In another general aspect, there is provided saroglitazar free acid of Formula (IA) having a chiral purity of at least about 98% by area percentage of HPLC. In particular, saroglitazar free acid having a chiral purity of at least about 99%, more particularly, a purity of at least about 99.5%, further more particularly, a purity of at least about 99.8%, most particularly, a purity of at least about 99.9% by area percentage of HPLC.

In another general aspect, there is provided an amorphous form of saroglitazar magnesium substantially free from residual solvents.

In another general aspect, there is provided a pharmaceutical composition comprising saroglitazar free acid of Formula (IA) together with one or more pharmaceutically acceptable carriers, excipients or diluents.

BRIEF DESCRIPTION OF THE ACCOMPANYING DRAWINGS

FIG. 1 discloses the X-ray diffractogram (XRD) of substantially amorphous form of saroglitazar magnesium as per example-1.

Figure 2:
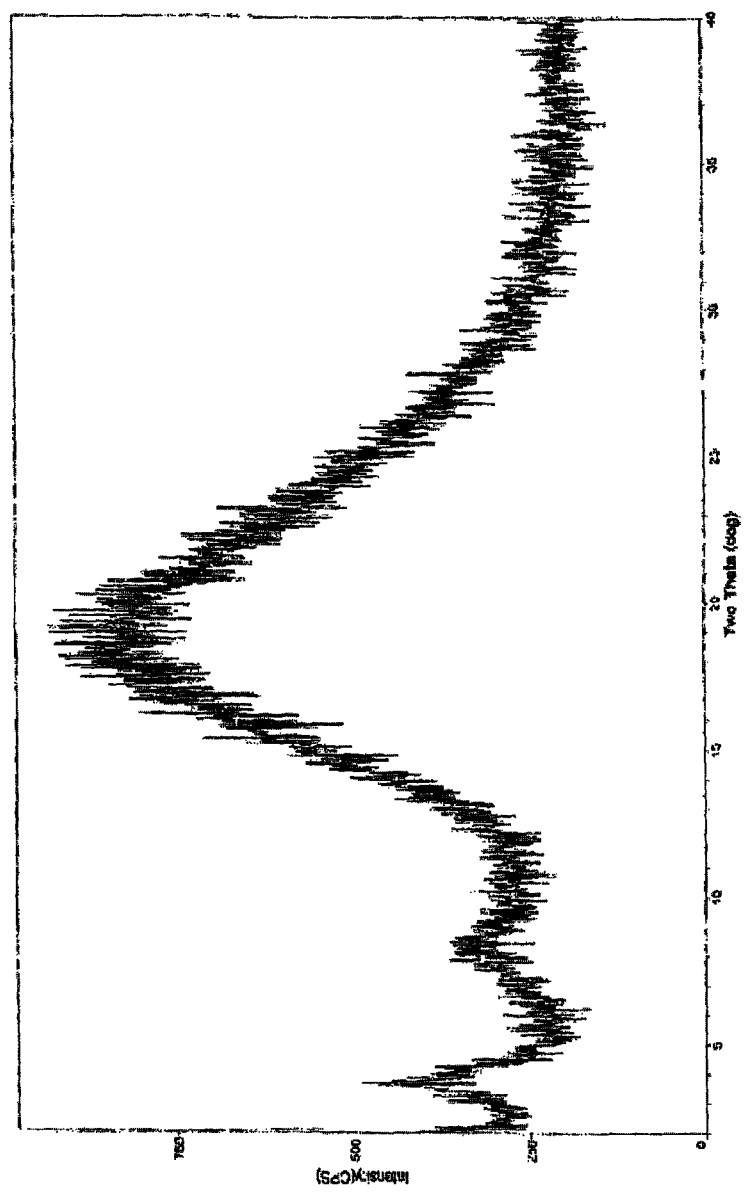

FIG. 2 discloses the X-ray diffractogram (XRD) of an amorphous form of saroglitazar magnesium as per example-2.

Figure 3:
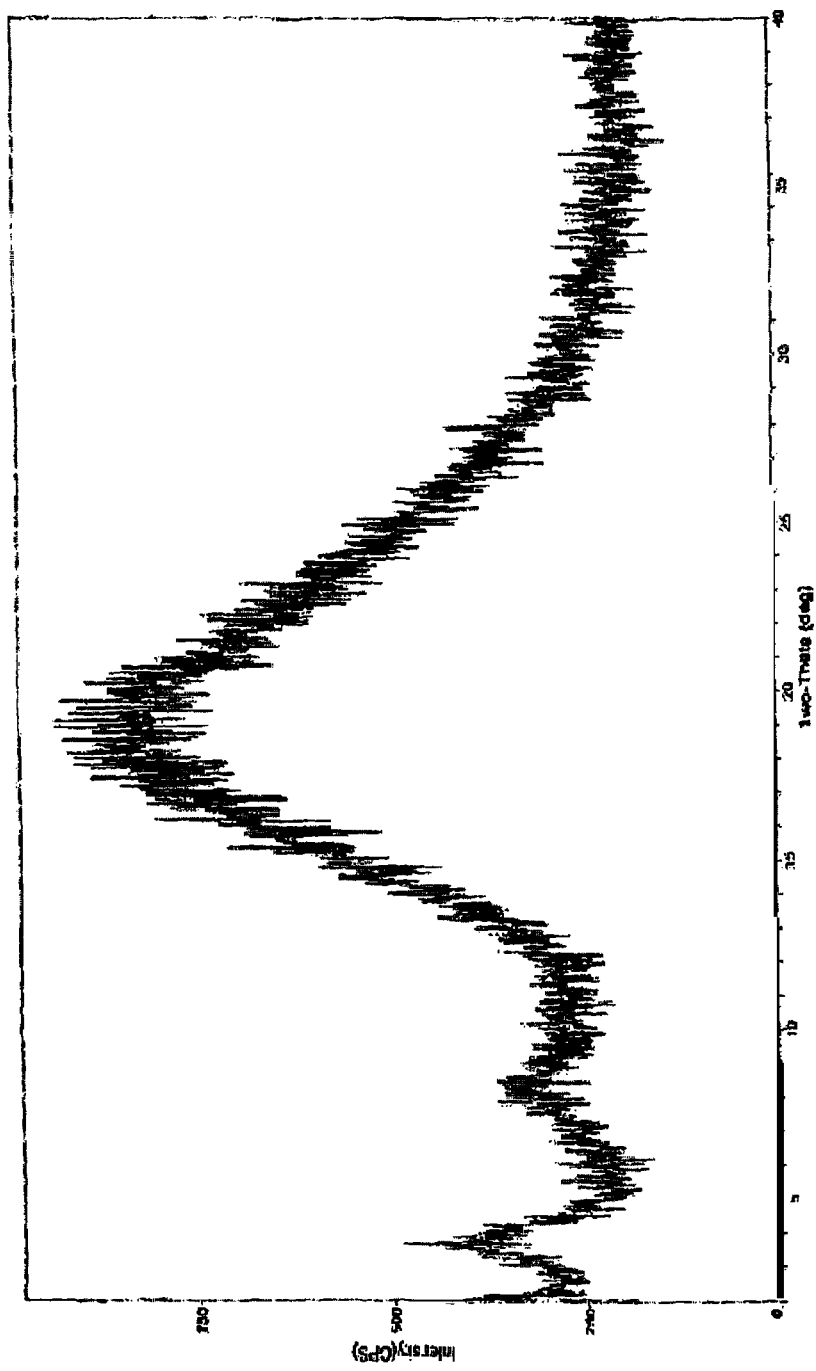

FIG. 3 discloses the X-ray diffractogram (XRD) of an amorphous form of saroglitazar magnesium as per example-3.

Figure 4:
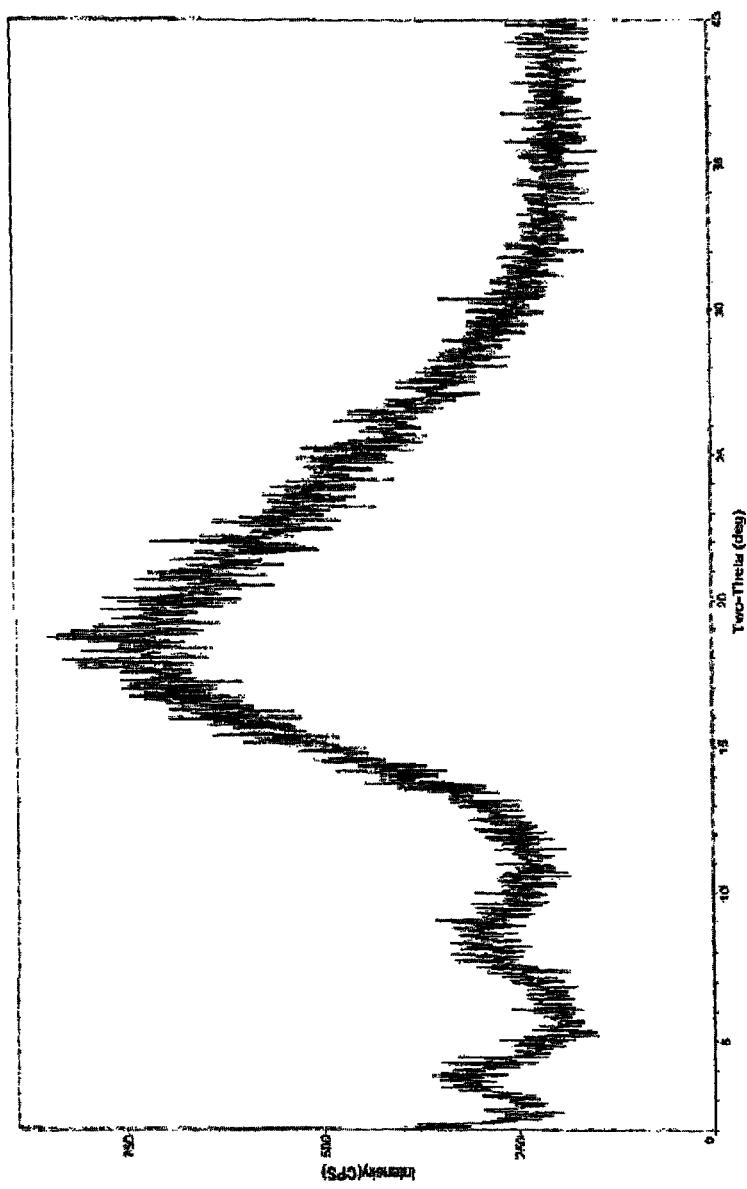

FIG. 4 discloses the X-ray diffractogram (XRD) of an amorphous form of saroglitazar magnesium as per example-4.

FIG. 5 discloses the X-ray diffractogram (XRD) of an amorphous form of saroglitazar free acid as per example-5.

DETAILED DESCRIPTION OF THE INVENTION

The above and other objects of the present invention are achieved by the process of the present invention, which leads to an amorphous form of saroglitazar magnesium suitable for pharmaceutical use. The invention provides a process for preparation of an amorphous form of saroglitazar magnesium suitable for development of finished formulations.

Optionally, the solution, prior to any solids formation, can be filtered to remove any undissolved solids, solid impurities prior to removal of the solvent. Any filtration system and filtration techniques known in the art can be used.

All ranges recited herein include the endpoints, including those that recite a range "between" two values. Terms such as "about", "generally", "substantially," and the like are to be construed as modifying a term or value such that it is not an absolute. This includes, at very least, the degree of expected experimental error, technique error and instrument error for a given technique used to measure a value.

The term "substantially free" means residual solvents within the permissible ICH limits suitable for pharmaceutical preparations. For example but not limited to less than 0.5%, particularly less than 0.3% or more particularly less than 0.2%.

The terms herein below are interchangeable and used in the description:
"DMF" refers to N,N-dimethylforamide.
"DMAc" refers to N,N-dimethylacetamide.
"DMSO" refers to N,N-dimethylsulfoxide.
"NMP" refers to N-methylpyrrolidone.
"THF" refers to tetrahydrofuran.
"MTBE" refers to methyl tert-butyl ether.
"TEA" refers to triethylamine.
"TBA" refers to tert-butyl amine.
"DIPA" refers to diisopropyl amine.
"DIPEA" refers to diisopropyl ethylamine.
"DBU" refers to 1,8-diazabicyclo[5.4.0]undec-7-ene.
"DABCO" refers to 1,4-diazabicyclo[2.2.2]octane.
"DBN" refers to 1,5-Diazabicyclo[4.3.0]non-5-ene
"HPLC" refers to high performance liquid chromatography.

In one general aspect, there is provided saroglitazar free acid of Formula (IA) or its pharmaceutically acceptable salts, pharmaceutically acceptable solvates, pharmaceutically acceptable esters, stereoisomers, tautomers, analogs and derivatives thereof.

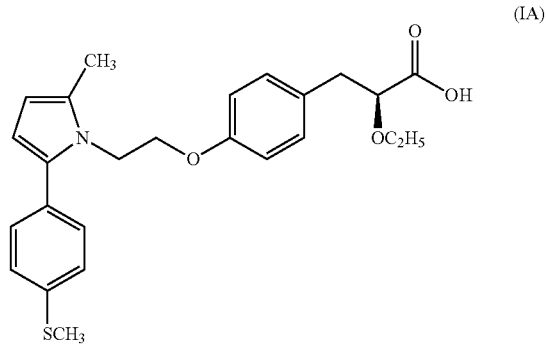 [SMILES: CCO[C@@H](Cc1ccc(OCCn2c(C)ccc2-c2ccc(SC)cc2)cc1)C(=O)O]

(IA)

In general, the pharmaceutically acceptable salt comprises of alkali or alkaline earth metal salts selected from lithium, barium, strontium, and zinc; or ammonium salt; or organic amines salts selected from methylamine, dimethylamine, ethylamine, diethylamine, 1,2-ethanediamine, n-propylamine, isopropylamine, diisopropylamine, N-methyl isopropylamine, n-butylamine, t-butylamine, 2-butamine, 1,2-ethanediamine, N-methylglucamine, N,N,N-trimethylethanolamine hydroxide (choline), tromethamine, cyclohexylamine, N-methylcyclohexylamine, guanidine, N-(4-aminobutyl) guanidine, dicyclohexylamine, benzenemethanamine, ethanolamine, diethanolamine, tris(hydroxymethyl)-methylamine, hydroxylamine, methanaminium, benzylamine, N-methyl-benzylamine, N-ethylbenzylamine, 4-methoxybenzylamine, pyrrolidine, piperidine, piperazine, morpholine, 2-aminopyrimidine, L-alanine, L-lysine, D-lysine, L-arginine, L-histidine, L-threonine, 2-thiopheneethanamine, (2S)-3,3-dimethyl-2-butanamine, cyclo pentanamine, and cycloheptanamine.

In another general aspect, there is provided an amorphous form of saroglitazar free acid of Formula (IA).

In another general aspect, there is provided an amorphous form of saroglitazar magnesium of Formula (I).

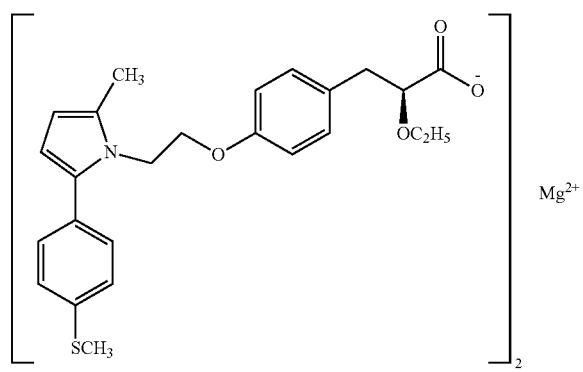

(I)

In another general aspect, there is provided an amorphous form of saroglitazar magnesium having a purity of at least about 98% by area percentage of HPLC and less than about 0.5% residual solvent.

In another general aspect, there is provided a process for the preparation of an amorphous form of saroglitazar magnesium of Formula (I),

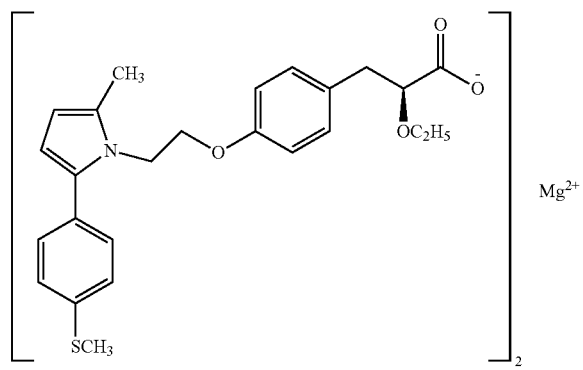

(I)

the process comprising:

(a) dissolving saroglitazar magnesium of Formula (I) in one or more organic solvents to obtain a solution, (b) adding the solution in one or more of anti-solvent at temperature from about −80° C. to about 150° C. to obtain saroglitazar magnesium of Formula (I); and (c) obtaining the amorphous saroglitazar magnesium by removal of anti-solvent.

In general, the organic solvent comprises one or more of alcohols selected from methanol, ethanol, isopropanol, 2-propanol, 1-butanol, and t-butyl alcohol; ketones selected from acetone, butanone, and methyl isobutyl ketone; esters selected from ethyl acetate, isopropyl acetate, t-butyl acetate, and isobutyl acetate; chlorinated hydrocarbons selected from methylene dichloride, ethylene dichloride, and chlorobenzene; or mixture thereof. In particular, methylene dichloride is used.

The anti-solvent comprises one or more of hydrocarbons selected from pentane, hexane, heptane, and cyclohexane; ethers selected from tetrahydrofuran, 1,4-dioxane, diisopropyl ether, diethyl ether, and methyl tertbutyl ether. In particular, the anti-solvent is n-heptane.

In one of the preferred aspect, the anti-solvent may also be a mixture of one or more of suitable solvents. In particular, n-heptane may be mixed with one or more of esters selected from ethyl acetate, propyl acetate, isopropyl acetate, and butyl acetate. In particular, the anti-solvent is mixture of n-heptane and n-butyl acetate.

In general, the solution of saroglitazar magnesium of Formula (I) is added to the mixture of anti-solvent at a temperature from about −80° C. to about 150° C. In particular, the addition is done at about −40° C. or at about 90° C. followed by maintaining the reaction mixture for about 30 minutes to at least 2 hours at the same temperature.

In general, when the addition is performed at −40° C., the amorphous form of saroglitazar magnesium of Formula (I) is obtained by filtration, washing the wet-cake with n-heptane and drying. Alternatively, when the addition is performed at 90° C., the amorphous form of saroglitazar magnesium of Formula (I) is obtained by cooling the reaction mixture to 50° C., stirring for at least 30 minutes and filtering. The wet-cake is washed with n-heptane and drying.

In another preferred aspect, the amorphous form of saroglitazar magnesium of Formula (I) is thus obtained by removing the anti-solvent by filtration, washing and drying.

In general, the amorphous form of saroglitazar magnesium of Formula (I) is characterized by X-ray powder diffraction patter substantially as depicted in FIG. 2-4.

In another general aspect, there is provided a process for the preparation of an amorphous form of saroglitazar magnesium of Formula (I),

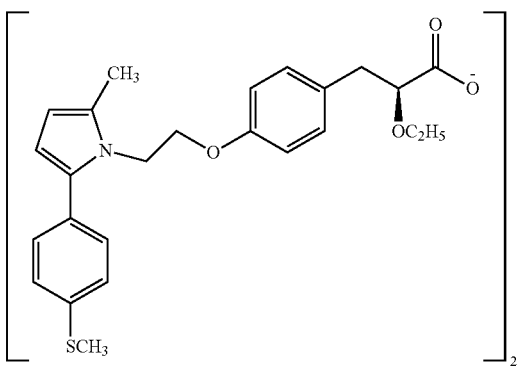

the process comprising:
(a) reacting a hydroxy compound (A) with a mesylate compound (A1) in one or more organic solvents in the presence of a base to obtain an alkoxy ester compound of Formula (II),

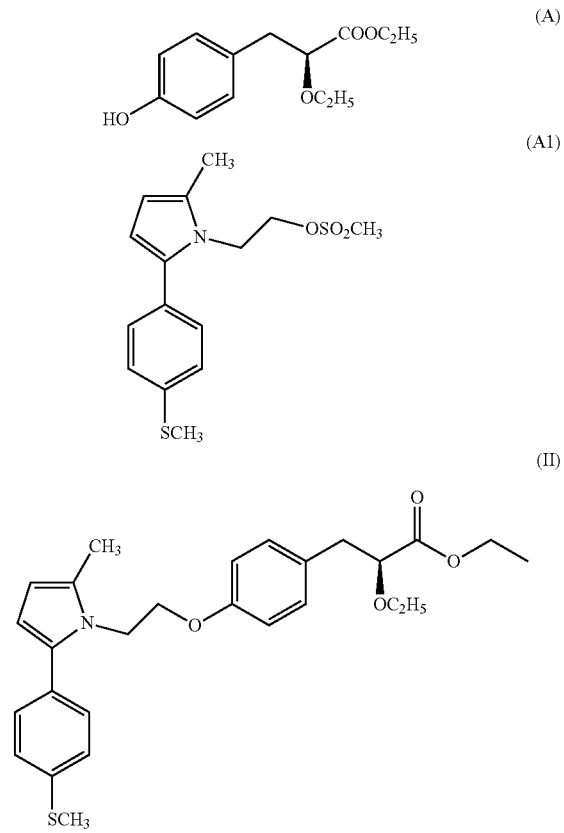

(b) hydrolyzing the alkoxy ester compound of Formula (II) with a base in one or more organic solvents to obtain a reaction mixture,
(c) washing the reaction mixture with one or more organic solvents to obtain aqueous layer,
(d) treating the aqueous layer with magnesium source to obtain saroglitazar magnesium solution,
(e) removal of solvent from the solution to obtain saroglitazar magnesium residue; and
(f) addition of one or more of anti-solvent to the residue followed by removal of anti-solvent to obtain the amorphous form of saroglitazar magnesium of Formula (I).

In general, the organic solvent comprises one or more of alcohols selected from methanol, ethanol, isopropanol, 2-propanol, 1-butanol, and t-butyl alcohol; ketones selected from acetone, butanone, and methyl isobutyl ketone; esters selected from ethyl acetate, isopropyl acetate, t-butyl acetate, and isobutyl acetate; chlorinated hydrocarbons selected from methylene dichloride, ethylene dichloride, and chlorobenzene; hydrocarbons selected from pentane, hexane, heptane, and cyclohexane; ethers selected from tetrahydrofuran, 1,4-dioxane, diisopropyl ether, diethyl ether, and methyl tert-butyl ether; or mixture thereof. In particular, the mixture of cyclohexane and tetrahydrofuran may be used.

In general, the base comprises one or more of sodium hydroxide, potassium hydroxide, lithium hydroxide, calcium hydroxide, sodium carbonate, potassium carbonate, sodium bicarbonate, potassium bicarbonate, sodium hydride, potassium hydride, potassium tert-butoxide, and sodium pentoxide. In particular, potassium carbonate is used. The base may be preferably anhydrous.

Optionally, the reaction may be catalyzed by a phase transfer catalyst. The phase transfer catalyst comprises one or more of tetrabutyl ammonium bromide (TBAB), tetrabutyl ammonium iodide (TBAI), benzyl triethyl ammonium chloride (TEBAC), polyethylene glycol (PEG-200, 400, 600, 800, 1000), crown ethers like 12-crown-4, 15-crown-5, 18-crown-6, dibenzo-18-crown-6, and diaza-18-crown-6. In particular, the phase transfer catalyst may be 18-crown-6.

In general, the reaction of a hydroxy compound (A) and a mesylate compound (A1) may be performed under heating at 35° C. to about reflux temperature of solvents. In particular, the reaction may be heated at 75° C. to 85° C. till the completion of the reaction. The reaction may be heated for about 25 hours to about 40 hours. In particular, for about 36 hours.

In another general aspect, the obtained alkoxy ester (II) may be proceeded further without isolating. Therefore, the alkoxy ester (II) may be further hydrolyzed in-situ.

The base for hydrolyzing the alkoxy ester (II) comprises one or more of sodium hydroxide, potassium hydroxide, lithium hydroxide, calcium hydroxide, sodium carbonate, potassium carbonate, sodium bicarbonate, potassium bicarbonate, sodium hydride, potassium hydride, potassium tert-butoxide, and sodium pentoxide. In particular, sodium hydroxide may be used.

In general, the reaction mixture after hydrolysis of alkoxy ester compound of Formula (II) may be washed with one or more organic solvents. The organic solvent comprises one or more of water, methanol, ethanol, isopropanol, 2-propanol, 1-butanol, t-butyl alcohol, acetone, butanone, methyl isobutyl ketone, ethyl acetate, isopropyl acetate, isobutyl acetate, t-butyl acetate, n-butyl acetate, methylene dichloride, ethylene dichloride, and chlorobenzene, or mixture thereof. In particular mixture of water and n-butyl acetate may be used.

The separated aqueous layer is treated with suitable magnesium source to obtain saroglitazar magnesium. In general, the magnesium source comprises one or more of magnesium hydroxide, magnesium methoxide, magnesium acetate; magnesium chloride, and magnesium metal. In particular, the magnesium source may be magnesium acetate tetrahydrate in form of its solution in water.

The separated layer after the formation of saroglitazar magnesium of Formula (I) may be further diluted with water and distilled to remove the water completely below 75° C. under vacuum to obtain the residue.

In general, the residue thus obtained is treated with one or more of anti-solvent comprises of hydrocarbons selected from pentane, hexane, heptane, and cyclohexane; ethers selected from tetrahydrofuran, 1,4-dioxane, diisopropyl ether, diethyl ether, and methyl tertbutyl ether. In particular, the anti-solvent is cyclohexane.

In the preferred aspect, the amorphous form of saroglitazar magnesium of Formula (I) may be obtained by removal of cyclohexane by distillation under vacuum and drying the product.

The product thus obtained may be dried under vacuum tray drier, sieved and milled to obtained suitable particle size range. The milled product may be further dried till constant weight may be obtained to obtain the amorphous form of saroglitazar magnesium (I) substantially free from residual solvents.

In general, the sieving of product may be done through 0.5 sieve followed by milling. Examples of such milling include various makes of ball mills, roller mills, gyratory mills, multi-mills, Jet-mills, and the like. In a preferred aspect, a mill such as a Micros Super Fine Mill (available from Nara Machinery Co. Ltd or Tokyo, Japan), Multi-Mill Sr. No. G. 1.132 (available from Grooves International Pharmaceutical & Chemical Machinery), Jet-Mill from Midas Micronizer M-100 Aerosol (No. 154/07-08 (available from microtech Enginering Company) or a common mixer grinder can be used. Alternatively another commercially available milling machine can be used.

In another general aspect, there is provided an amorphous form of saroglitazar magnesium having a particle size distributions having D(10) of about 50 μm or less, D(50) of about 200 μm or less and D(90) of about 400 μm or less; or any combination thereof. In particular, there another general aspect, there is provided an amorphous form of saroglitazar magnesium having particle size distributions having D(10) of about 20 μm or less, (D50) of about 100 μm or less, and D(90) of about 200 μm or less, or any combination thereof.

In another general aspect, there is provided an amorphous form of saroglitazar magnesium having a purity of at least about 98% by area percentage of HPLC. In particular, saroglitazar magnesium having a purity of at least about 99%, a purity of at least about 99.5%, a purity of at least about 99.9% by area percentage of HPLC.

In another general aspect, there is provided an amorphous form of saroglitazar magnesium having a chiral purity of at least about 98% by area percentage of HPLC. In particular, saroglitazar magnesium having a chiral purity of at least about 99%, a chiral purity of at least about 99.5%, a chiral purity of at least about 99.9% by area percentage of chiral HPLC.

In another general aspect, there is provided an amorphous form of saroglitazar magnesium substantially free from residual solvents.

In another general aspect, there is provided a process for the preparation of saroglitazar free acid of Formula (IA) or its pharmaceutically acceptable salts thereof,

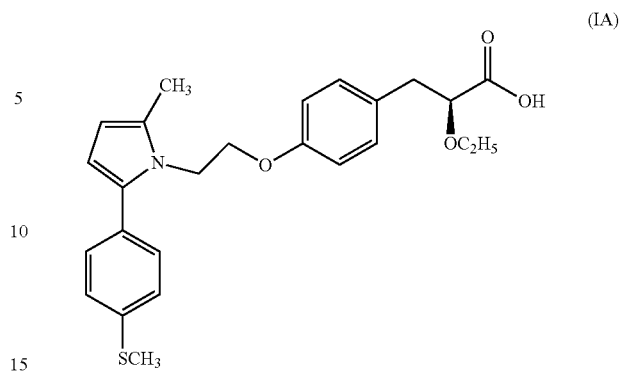

the process comprising:
(a) reacting hydroxy compound (A) with mesylate compound (A1) in one or more of suitable organic solvent in the presence of a base to obtain alkoxy ester compound of Formula (II),

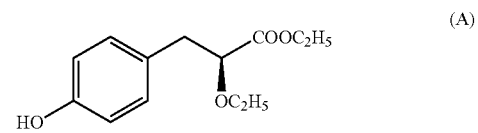

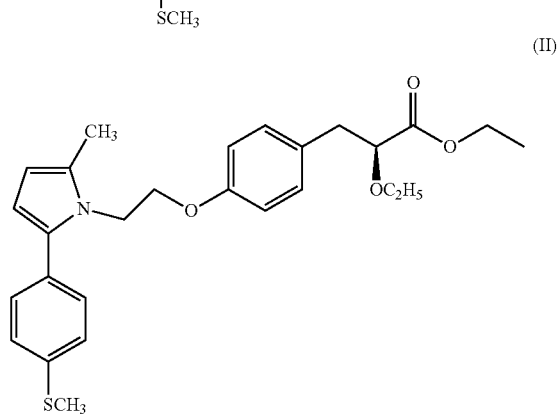

(b) hydrolyzing the alkoxy ester compound of Formula (II) with a base in one or more organic solvent to obtain reaction mixture,
(c) acidifying the reaction mixture with an acid to obtain saroglitazar free acid (IA) in reaction mixture,
(d) extracting the saroglitazar free acid (IA) in one or more organic solvents; and
(e) obtaining the saroglitazar free acid (IA) by removal of solvent.

In general, the organic solvent comprises one or more of alcohols selected from methanol, ethanol, isopropanol, 2-propanol, 1-butanol, and t-butyl alcohol; ketones selected from acetone, butanone, and methyl isobutyl ketone; esters selected from ethyl acetate, isopropyl acetate, t-butyl acetate, n-butyl acetate and isobutyl acetate; chlorinated hydrocarbons selected from methylene dichloride, ethylene dichloride, and chlorobenzene; hydrocarbons selected from pentane, hexane, heptane, and cyclohexane; ethers selected from tetrahydrofuran, 1,4-dioxane, diisopropyl ether, diethyl ether, methyl tert-butyl ether, or mixture thereof. In particular, the mixture of cyclohexane and tetrahydrofuran is used.

In general, the base comprises one or more of sodium hydroxide, potassium hydroxide, lithium hydroxide, calcium hydroxide, sodium carbonate, potassium carbonate, sodium bicarbonate, potassium bicarbonate, sodium hydride, potassium hydride, potassium tert-butoxide, and sodium pentoxide. More particularly, potassium carbonate may be used. The base may be preferably anhydrous.

Optionally, the reaction may be catalyzed by phase transfer catalyst. The phase transfer catalyst comprises one or more of tetrabutyl ammonium bromide (TBAB), tetrabutyl ammonium iodide (TBAI), benzyl triethyl ammonium chloride (TEBAC), polyethylene Glycol (PEG-200, 400, 600, 800, 1000), crown ethers like 12-crown-4, 15-crown-5, 18-crown-6, dibenzo-18-crown-6, and diaza-18-crown-6.

In general, the reaction of a hydroxy compound (A) and a mesylate compound (A1) may be performed under heating at 35° C. to about reflux temperature of solvents. In particular, the reaction may be heated at 75° C. to 85° C. till the completion of the reaction. The reaction may be heated for about 25 hours to about 40 hours. In particular, for about 36 hours.

In another general aspect, the obtained alkoxy ester (II) may be proceeded further without isolating. Therefore, the alkoxy ester (II) may be further hydrolyzed in-situ.

The suitable base for hydrolyzing alkoxy ester (II) comprises one or more of sodium hydroxide, potassium hydroxide, lithium hydroxide, calcium hydroxide, sodium carbonate, potassium carbonate, sodium bicarbonate, potassium bicarbonate, sodium hydroxide, and potassium hydride. In particular, sodium hydroxide may be used.

In general, the acid for acidifying the reaction mixture comprises one or more of hydrochloric acid, hydrobromic acid, sulfuric acid, nitric acid, phosphoric acid, formic acid, oxalic acid, acetic acid, and triflouroacetic acid. In particular, hydrochloric acid or acetic acid may be used.

In general, the saroglitazar free acid (IA) is obtained by extracting with one or more of organic solvents followed by removal of the solvent. The residue may be treated with an anti-solvent to isolate saroglitazar free acid (IA).

In general, the organic solvent for extraction comprises of methylene dichloride, dimethyl formamide, dimethyl acetamide, tetrahydrofuran, toluene, ethyl acetate, n-butyl acetate, methanol, acetone, chloroform, and 1,4-dioxane. In particular, methylene dichloride may be used.

The solvent may be distilled under vacuum for the removal of solvent below 40° C. thereby to obtain residue. In general, the residue thus obtained may be treated with one or more of anti-solvent comprises of hydrocarbons selected from pentane, hexane, heptane, and cyclohexane; ethers selected from tetrahydrofuran, 1,4-dioxane, diisopropyl ether, diethyl ether, and methyl tertbutyl ether. In particular, the anti-solvent is cyclohexane.

In another general aspect, there is provided a process for the preparation of saroglitazar free acid of Formula (IA) or its pharmaceutically acceptable salts thereof,

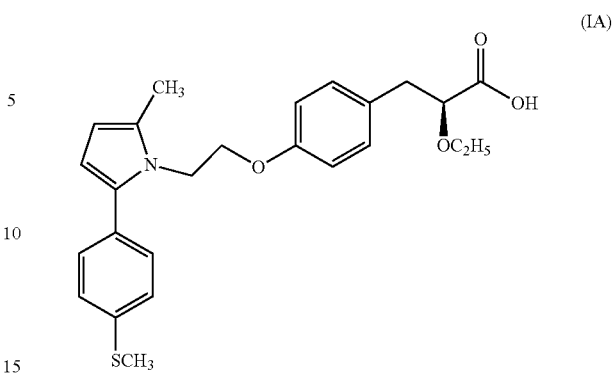

the process comprising:
(a) providing a solution of saroglitazar magnesium of Formula (I) in one or more organic solvents;
(b) adding a base in the solution to obtain a reaction mixture,
(c) acidifying the reaction mixture with an acid to obtain saroglitazar free acid (IA) in reaction mixture,
(d) extracting the saroglitazar free acid (IA) in one or more organic solvents; and
(e) obtaining the saroglitazar free acid (IA) by removal of solvent.

In general, the organic solvent comprises one or more of alcohols selected from methanol, ethanol, isopropanol, 2-propanol, 1-butanol, and t-butyl alcohol; ketones selected from acetone, butanone, and methyl isobutyl ketone; esters selected from ethyl acetate, isopropyl acetate, t-butyl acetate, and isobutyl acetate; chlorinated hydrocarbons selected from methylene dichloride, ethylene dichloride, and chlorobenzene; or mixture thereof. In particular alcohols may be used.

The base comprises one or more of sodium hydroxide, potassium hydroxide, lithium hydroxide, calcium hydroxide, sodium carbonate, potassium carbonate, sodium bicarbonate, potassium bicarbonate, sodium hydroxide, potassium hydride, potassium tert-butoxide, and sodium pentoxide. In particular, sodium hydroxide may be used.

In general, the acid comprises one or more of hydrochloric acid, hydrobromic acid, sulfuric acid, nitric acid, phosphoric acid, formic acid, oxalic acid, acetic acid, and triflouroacetic acid. In particular, the hydrochloric acid may be used.

In general, the saroglitazar free acid (IA) is obtained by extracting with one or more of organic solvents followed by removal of the solvent. The residue may be treated with an anti-solvent to isolate saroglitazar free acid (IA).

In general, the organic solvent for extraction comprises of methylene dichloride, dimethyl formamide, dimethyl acetamide, tetrahydrofuran, toluene, ethyl acetate, n-butyl acetate, methanol, acetone, chloroform, and 1,4-dioxane.

The solvent may be distilled under vacuum for the removal of solvent below 40° C. thereby to obtain residue. In general, the residue thus obtained may be treated with one or more of anti-solvent comprises of hydrocarbons selected from pentane, hexane, heptane, and cyclohexane; ethers selected from tetrahydrofuran, 1,4-dioxane, diisopropyl ether, diethyl ether, and methyl tertbutyl ether. In particular, the anti-solvent is cyclohexane.

In another general aspect, there is provided saroglitazar free acid of Formula (IA) having a purity of at least about 98% by area percentage of HPLC. In particular, saroglitazar free acid having a purity of at least about 99%, a purity of at least about 99.5%, a purity of at least about 99.9% by area percentage of HPLC.

In another general aspect, there is provided saroglitazar free acid of Formula (IA) having a chiral purity of at least about 98% by area percentage of chiral HPLC. In particular, saroglitazar free acid having a chiral purity of at least about 99%, a chiral purity of at least about 99.5%, a chiral purity of at least about 99.9% by area percentage of chiral HPLC.

In another general aspect, there is provided a process for the preparation of saroglitazar magnesium of Formula (I) comprising preparing saroglitazar free acid of Formula (IA) or its pharmaceutically acceptable salts thereof and convening it to saroglitazar magnesium of Formula (I).

In general, the pharmaceutically acceptable salt comprises of alkali or alkaline earth metal salts selected from lithium, barium, strontium, and zinc; or ammonium salt or organic amines salts selected from methylamine, dimethylamine, ethylamine, diethylamine, 1,2-ethanediamine, n-propylamine, isopropylamine, diisopropyl amine, N-methylisopropylamine, n-butylamine, t-butylamine, 2-butamine, 1,2-ethanediamine, N-methylglucamine, N,N,N-trimethylethanolamine hydroxide (choline), tromethamine, cyclohexylamine, N-methylcyclohexylamine, guanidine, N-(4-aminobutyl) guanidine, dicyclohexylamine, benzenemethanamine, ethanolamine, diethanolamine, tris(hydroxymethyl) methylamine, hydroxylamine, methanaminium, benzylamine, N-methylbenzylamine, N-ethylbenzylamine, 4-methoxybenzylamine, pyrrolidine, piperidine, piperazine, morpholine, 2-amino pyrimidine, L-alanine, L-lysine, D-lysine, L-arginine, L-histidine, L-threonine, 2-thiopheneethanamine, (2S)-3,3-dimethyl-2-butanamine, cyclo pentanamine, and cycloheptanamine.

In another general aspect, there is provided a pharmaceutical composition comprising an amorphous form of saroglitazar magnesium of Formula (I) having particle size distributions having D(10) of about 20 μm or less, (D50) of about 100 μm or less, and D(90) of about 200 μm or less, or any combination thereof.

In another general aspect, there is provided a pharmaceutical composition comprising saroglitazar free acid of Formula (IA) together with one or more pharmaceutically acceptable carriers, excipients or diluents.

Powder X-ray Diffraction of amorphous saroglitazar magnesium (I) and an amorphous form of saroglitazar free acid (IA) can be obtained under following conditions.

Powder X-Ray Diffraction:

X-ray powder diffraction spectrum was observed on a MF 2100 2KW X-ray Powder diffractometer of make Rigaku or equivalent having a Copper Kα-radiation at a voltage of 40 kV and 30 mA. Approximately 150 mg sample was gently flattened on a quartz plate without further processing (e.g. Grinding and sieving) and scanned from 4° to 40° at 0.010° sampling width and 4.000° per minute.

In another general aspect, saroglitazar magnesium may be prepared by the reaction scheme-1, which is also the scope of the present invention.

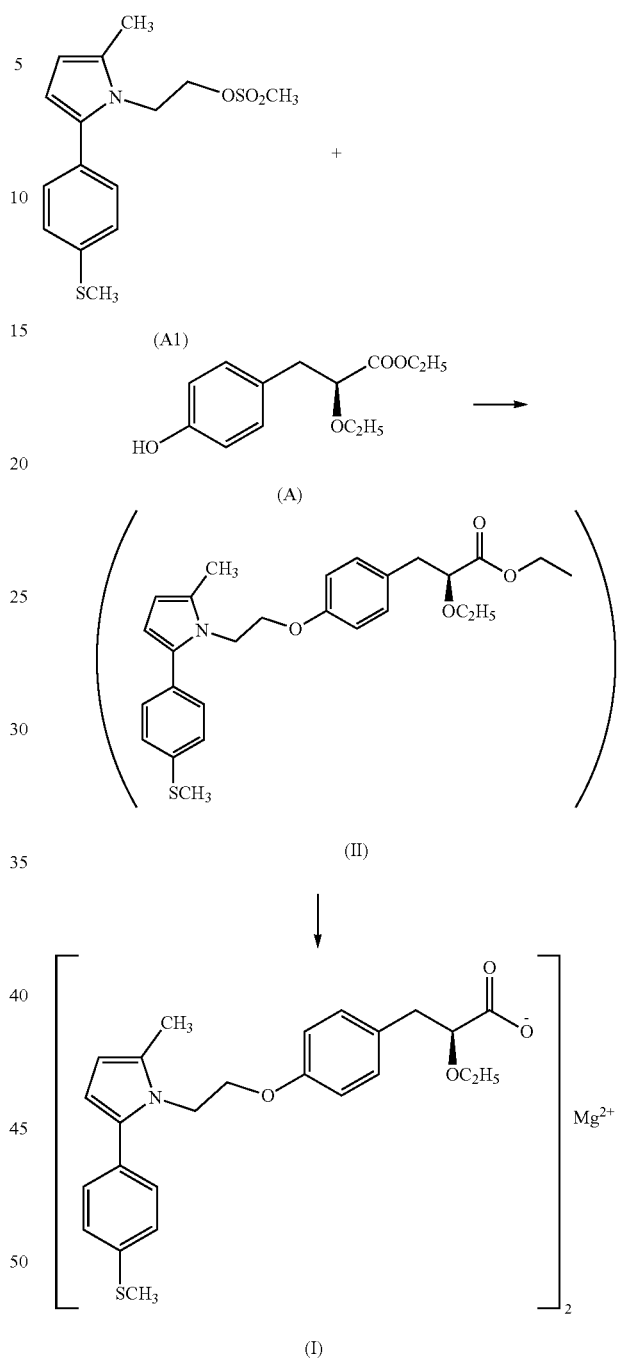

Scheme-1

The invention also encompasses pharmaceutical compositions comprising saroglitazar of the invention. As used herein, the term "pharmaceutical compositions" includes pharmaceutical Formulations like tablets, pills, powders, liquids, suspensions, emulsions, granules, capsules, suppositories, or injection preparations.

In another general aspect, there is provided a pharmaceutical composition comprising an amorphous form saroglitazar magnesium of Formula (I) together with one or more pharmaceutically acceptable carriers, excipients or diluents.

The present invention is further illustrated by the following example which is provided merely to be exemplary of the invention and do not limit the scope of the invention. Certain modification and equivalents will be apparent to those skilled in the art and are intended to be included within the scope of the present invention.

EXAMPLES

Example-1

Preparation of Saroglitazar Magnesium (I)
In a 5 Liter three necked round bottom flask equipped with nitrogen atmosphere facility, mechanical stirrer, thermometer and an addition funnel, 2-ethoxy-3-(4-hydroxy-phenyl)-propionic acid ethyl ester (A) (100.0 g) and cyclohexane (1300.0 ml) were charged and reaction mixture was heated to 45° to 55° C. Potassium carbonate (58.0 g) was added and stirred for 30 min. methanesulfonic acid 2-[2-methyl-5-(4-methylsulfanyl-phenyl)-pyrrol-1-yl]-ethyl ester (A1) (150.24 g) and THF (200.0 ml) were added and heated to 75° C. to 85° C. for 36 hour. The reaction mixture was cooled to 25° to 35° C. and water (1000.0 ml) was added and stirred for 15 min. The separated aqueous layer was treated with cyclohexane (200.0 ml) and stirred for 15 min. The organic layers were combined and washed with caustic solution (600.0 ml). The separated organic layer was washed with water (600.0 ml) and characoalized with (5.0 g) charcoal and stirred for 30 min and filtered. The filtrate was distilled to remove cyclohexane and the residue was collected (residue-A). The residue-A as obtained was treated with ethanol (400.0 ml) and stirred for 15 min. Sodium hydroxide 20.14 g solution in water (200.0 ml) was added and the reaction mixture was stirred for 3 hours. The reaction mixture was diluted with water (1800.0 ml) and stirred for 15 min. The separated aqueous layer was washed with n-butyl acetate. The separated aqueous layer was added magnesium acetate tetrahydrate solution (90.0 g) in water (100.0 ml) and stirred for 1 hour. The aqueous layer was extracted with methylene dichloride (200 ml). The separated organic layer was washed with sodium chloride solution and charcoalized. The charcoalized solution was filtered and filtrate was distilled to remove methylene dichloride completely. The residue was diluted with methylene dichloride (1000 ml) and stirred for 30 min. The organic solution was added into n-heptane (1500 mL) and stirred for 3 hours. The product was filtered and washed with n-heptane and dried in vacuum tray dryer at 25° C. to 30° C. for 3 hours. The product was sieved through 0.5 mm sieve and milled through jet-milled. The product was further dried in vacuum tray drier at 40° C. to 50° C. for 6 hours followed by drying at 55° C. to 65° C. for 40 hours to obtain substantially amorphous saroglitazar magnesium (I). The compound is characterized by x-ray power diffraction (FIG. 1).

Example-2

Preparation of Amorphous Saroglitazar Magnesium (I)
In a 250 mL three necked round bottom flask equipped with nitrogen atmosphere facility, mechanical stirrer, thermometer and an addition funnel, saroglitazar magnesium (5 g) obtained in example-1 and methylene dichloride (50 mL) were taken at 25° C. and stirred to prepare the solution-A. In another 250 mL three necked round bottom flask equipped with nitrogen atmosphere facility, mechanical stirrer, thermometer and an addition funnel, the mixture of n-butyl acetate (50 mL) and n-heptane (1000 mL) was prepared and heated at 85° C. to 90° C. The solution-A was added and stirred for 30 minutes. The reaction mixture was cooled to 50° C. and stirred for further 30 minutes. The product was filtered and washed with n-heptane and dried in vacuum tray dryer to obtain amorphous saroglitazar magnesium (I) having 99% HPLC purity and 99.5% chiral purity. The compound is characterized by x-ray power diffraction (FIG. 2).

Example-3

Preparation of Amorphous Saroglitazar Magnesium (I)
In a 250 mL three necked round bottom flask equipped with nitrogen atmosphere facility, mechanical stirrer, thermometer and an addition funnel, saroglitazar magnesium (5 g) obtained in example-1 and methylene dichloride (50 mL) were taken at 25° C. and stirred to prepare the solution-A. In another 250 mL three necked round bottom flask equipped with nitrogen atmosphere facility, mechanical stirrer, thermometer and an addition funnel, the mixture of butyl acetate (50 mL) and n-heptane (1000 mL) was prepared and cooled to −40° C. The solution-A was added and stirred for 30 minutes. The product was filtered and washed with n-heptane and dried in vacuum tray dryer to obtain amorphous saroglitazar magnesium (I). The compound is characterized by x-ray power diffraction (FIG. 3).

Example-4

Preparation of Amorphous Saroglitazar Magnesium (I)
In a 250 mL three necked round bottom flask equipped with nitrogen atmosphere facility, mechanical stirrer, thermometer and an addition funnel, residue-A (10 g) obtained in example-1 and ethanol (20 mL) were added at 25° C. Sodium hydroxide (1.03 g solution in water 10 mL) was added and the reaction mixture was stirred for 3 hours. The reaction mixture was diluted with n-butyl acetate (40 mL) and water (100 mL) and stirred for 30 min. The separated aqueous layer was washed with n-butyl acetate. The separated aqueous layer was added magnesium acetate tetrahydrate solution (4.58 g) in water (10 mL) and stirred for 1 hour. The aqueous layer was diluted with water (30 mL) and distilled to remove water completely under vacuum below 75° C. The residue was triturated with cyclohexane (50 mL) and further distilled under vacuum. The product thus obtained was dried in vacuum tray dryer to obtain amorphous saroglitazar magnesium (I). The compound is characterized by x-ray power diffraction (FIG. 4).

Example-5

Preparation of Amorphous Saroglitazar Free Acid (IA)
In a 250 mL three necked round bottom flask equipped with nitrogen atmosphere facility, mechanical stirrer, thermometer and an addition funnel, residue-A (10 g) obtained in example-1 and ethanol (20 mL) were added at 25° C. Sodium hydroxide (1.03 g solution in water 10 mL) was added and the reaction mixture was stirred for 3 hours. The reaction mixture was diluted water (100 mL), acidified with hydrochloric acid stirred for 60 min. The reaction mixture was extracted with methylene dichloride (50 mL) and washed with water (20 mL). The methylene dichloride was complete removed by distillation under vacuum below 40° C. to obtain the residue. The residue was triturated with cyclohexane (50 mL) and further distilled under vacuum. The product thus obtained was dried in vacuum tray dryer to obtain amorphous saroglitazar free acid (IA) having 99.13% HPLC purity and 99.5% chiral purity. The compound is characterized by x-ray power diffraction (FIG. 5).

Example-6

Preparation of Amorphous Saroglitazar Free Acid (IA)

In a 250 mL three necked round bottom flask equipped with nitrogen atmosphere facility, mechanical stirrer, thermometer and an addition funnel, saroglitazar magnesium (10 g) obtained in example-1 and ethanol (20 mL) were added at 25° C. Sodium hydroxide (1.03 g solution in water 10 mL) was added and the reaction mixture was stirred for 3 hours. The reaction mixture was diluted water (100 mL), acidified with hydrochloric acid stirred for 60 min. The reaction mixture was extracted with methylene dichloride (50 mL) and washed with water (20 mL). The methylene dichloride was complete removed by distillation under vacuum below 40° C. to obtain the residue. The residue was triturated with cyclohexane (50 mL) and further distilled under vacuum. The product thus obtained was dried in vacuum tray dryer to obtain amorphous saroglitazar free acid (IA) having 99.5% HPLC purity and 99.8% chiral purity. The product thus obtained was dried in vacuum tray dryer to obtain amorphous saroglitazar free acid (IA).

Example-7

Preparation of Saroglitazar Phenyl Ethylamine Salt

In a 250 mL three necked round bottom flask equipped with nitrogen atmosphere facility, mechanical stirrer, thermometer and an addition funnel, residue-A obtained in example-1 and ethanol (400 mL) were stirred for 15 min. Sodium hydroxide 20.14 g solution in water (200.0 ml) was added and the reaction mixture was stirred for 3 hours. The reaction mixture was diluted with water (1800.0 ml) and stirred for 15 min. The separated aqueous layer was washed with isopropyl acetate (400 mL). The separated aqueous layer was diluted with isopropyl acetate (500 mL) and acidified with conc. HCl at adjust the pH 2-3. The separated aqueous layer was washed with isopropyl acetate. The combined organic layer was treated with (S)-(−)-phenyl ethylamine (55.94 g) and stirred for 2 hours at 25° C. and 30 min at 45° C. The reaction mixture was cooled to 0° C. and stirred for 2 hours, filtered and washed with isopropyl acetate. The wet-cake was dried to obtain saroglitazar phenyl ethylamine salt.

Example-8

Preparation of Saroglitazar Magnesium from Saroglitazar Phenyl Ethylamine Salt

In a 250 mL three necked round bottom flask equipped with nitrogen atmosphere facility, mechanical stirrer, thermometer and an addition funnel, saroglitazar phenyl ethylamine wet-cake obtained in example-7 and isopropyl acetate (800 mL) were added at 25° C. The reaction mixture was diluted with water (400.0 ml) and acidified with conc. HCl at adjust the pH 2-3. The separated aqueous layer was washed with isopropyl acetate. The combined organic layer was treated with sodium hydroxide solution (20.14 g) in water (200 mL) and stirred for 30 min. The separated aqueous layer was treated with magnesium acetate tetrahydrate (2.29 g) in water (5 mL) solution and stirred for 60 min. The reaction mixture was extracted with methylene dichloride (800 mL). The methylene dichloride was complete removed by distillation under vacuum below 40° C. to obtain the residue. The residue was diluted with methylene dichloride (50 ml) and stirred for 30 min. The organic solution was added into n-heptane (1500 mL) and stirred for 3 hours. The product was filtered and washed with n-heptane and dried in vacuum tray dryer at 25° C. to 30° C. for 3 hours. The product was sieved through 0.5 mm sieve and milled through jet-milled. The product was further dried in vacuum tray drier at 40° C. to 50° C. for 6 hours followed by drying at 55° C. to 65° C. for 40 hours to obtain substantially amorphous saroglitazar magnesium (I). The compound is characterized by x-ray power diffraction (FIG. 1).

Example-9

Preparation of Saroglitazar Magnesium from Saroglitazar Phenyl Ethylamine Salt

In a 250 mL three necked round bottom flask equipped with nitrogen atmosphere facility, mechanical stirrer, thermometer and an addition funnel, saroglitazar phenyl ethylamine (10 g) and ethanol (100 mL) were added at 25° C. The reaction mixture was heated to reflux to obtain clear solution. Magnesium acetate tetrahydrate (2.29 g) in water (5 mL) solution was added and stirred for 30 minutes. The reaction mixture was cooled to 25° C. and filtered. The wet-cake was washed with ethanol and dried in vacuum tray drier to obtain saroglitazar magnesium. The compound is characterized by x-ray power diffraction (FIG. 1).

While the present invention has been described in terms of its specific embodiments, certain modifications and equivalents will be apparent to those skilled in the art and are intended to be included within the scope of the present invention.

We claim:

1. A process for the preparation of an amorphous form of saroglitazar magnesium of Formula (I),

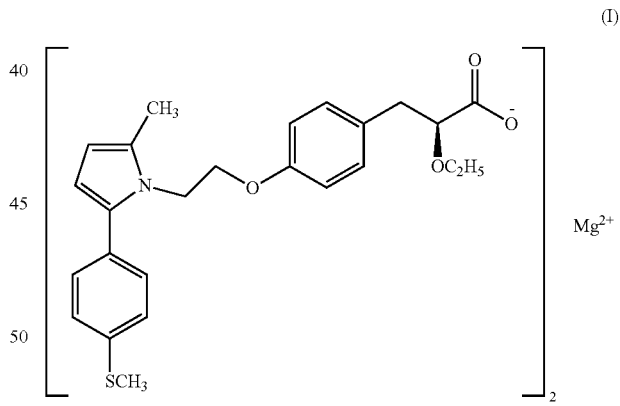

the process comprising:
(a) reacting a hydroxy compound (A) with a mesylate compound (A1) in a mixture of cyclohexane and tetrahydrofuran in the presence of a base to obtain an alkoxy ester compound of Formula (II),

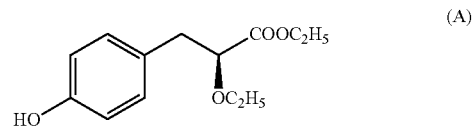

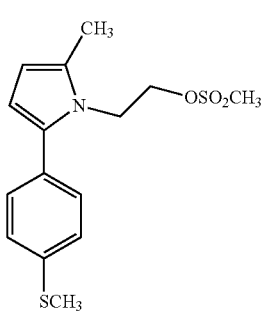
(A1)

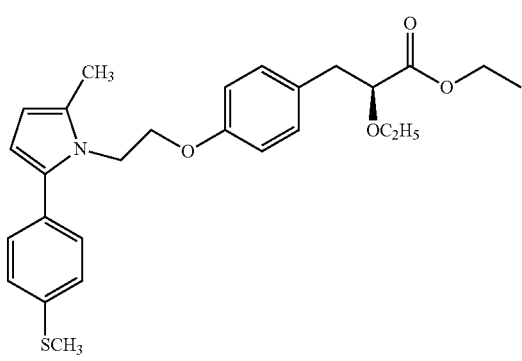
(II)

(b) hydrolyzing the alkoxy ester compound of Formula (II) with a base in one or more organic solvents to obtain a reaction mixture,
(c) washing the reaction mixture with water and one or more organic solvents, and obtaining a separated aqueous layer,
(d) treating the separated aqueous layer with a magnesium source to obtain a saroglitazar magnesium solution,
(e) removing water from the solution to obtain a saroglitazar magnesium residue; and
(f) adding one or more anti-solvent to the residue followed by removal of anti-solvent to obtain the amorphous form of saroglitazar magnesium of Formula (I).

2. The process according to claim 1, wherein the anti-solvent comprises one or more of pentane, hexane, heptane, cyclohexane, tetrahydrofuran, 1,4-dioxane, diisopropyl ether, diethyl ether, and methyl tertbutyl ether.

3. The process according to claim 1, wherein the base in step (a) comprises one or more of sodium hydroxide, potassium hydroxide, lithium hydroxide, calcium hydroxide, sodium carbonate, potassium carbonate, sodium bicarbonate, potassium bicarbonate, sodium hydroxide, potassium hydride, potassium tert-butoxide, and sodium pentoxide.

4. The process according to claim 1, wherein the magnesium source in step (d) comprises one or more of magnesium hydroxide, magnesium methoxide, magnesium acetate, magnesium chloride, and magnesium metal.

* * * * *